(12) United States Patent
Zhang

(10) Patent No.: US 10,588,586 B2
(45) Date of Patent: Mar. 17, 2020

(54) CARDIAC ANALYSIS BASED ON VESSEL CHARACTERISTICS

(71) Applicant: Siemens Medical Solutions USA, Inc., Malvern, PA (US)

(72) Inventor: Hongxuan Zhang, Palatine, IL (US)

(73) Assignee: Siemens Healthcare GmbH, Erlangen (DE)

( * ) Notice: Subject to any disclaimer, the term of this patent is extended or adjusted under 35 U.S.C. 154(b) by 1219 days.

(21) Appl. No.: 14/155,393

(22) Filed: Jan. 15, 2014

(65) Prior Publication Data

US 2014/0200461 A1 Jul. 17, 2014

Related U.S. Application Data

(60) Provisional application No. 61/753,024, filed on Jan. 16, 2013.

(51) Int. Cl.
*A61B 6/00* (2006.01)
*G06T 7/62* (2017.01)
*A61B 5/055* (2006.01)
*A61B 6/03* (2006.01)
*G01R 33/563* (2006.01)
*A61B 5/02* (2006.01)

(52) U.S. Cl.
CPC .............. *A61B 6/504* (2013.01); *A61B 6/481* (2013.01); *A61B 6/486* (2013.01); *A61B 6/507* (2013.01); *A61B 6/5217* (2013.01); *A61B 6/5288* (2013.01); *G06T 7/62* (2017.01); *A61B 5/02007* (2013.01); *A61B 5/055* (2013.01); *A61B 6/032* (2013.01); *A61B 6/037* (2013.01); *A61B 6/4441* (2013.01); *G01R 33/5635* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 5,151,856 A | 9/1992 | Halmann et al. |
| 6,580,016 B2 | 6/2003 | Teirstein et al. |
| 7,390,303 B2 | 6/2008 | Dafni |
| 7,534,209 B2 | 5/2009 | Abend |
| 7,559,894 B2 | 7/2009 | Mceowen |
| 7,609,814 B2 | 10/2009 | Baumgart |
| 7,620,501 B2 | 11/2009 | Tek et al. |
| 7,639,847 B2 | 12/2009 | Middleton et al. |
| 7,652,468 B2 | 1/2010 | Kruger et al. |

(Continued)

FOREIGN PATENT DOCUMENTS

IN 44/KOL/2011 A * 11/2012 ............... A61B 5/02

OTHER PUBLICATIONS

Faber et al. "Three-Dimensional Fusion of Coronary Arteries with Myocardial Perfusion Distribution: Clinical Validation", The Journal of Nuclear Medicine, vol. 45, No. 5, 2004.*

*Primary Examiner* — Carolyn A Pehlke
*Assistant Examiner* — Marjan Saboktakin

(57) ABSTRACT

A system and method includes reception of a first image of a blood vessel, reception of a second image of the blood vessel, determination of a first size of a region of the blood vessel based on the first image, determination of a second size of the region of the blood vessel based on the second image, and calculation of a parameter of the blood vessel based on the first size and the second size.

16 Claims, 9 Drawing Sheets

(56) References Cited

U.S. PATENT DOCUMENTS

| | | |
|---|---|---|
| 7,774,036 B2 | 8/2010 | Halldorsson et al. |
| 7,844,320 B2 | 11/2010 | Shahidi |
| 7,860,283 B2 | 12/2010 | Begelman et al. |
| 7,860,290 B2 | 12/2010 | Gulsun et al. |
| 7,873,194 B2 | 1/2011 | Begelan et al. |
| 7,940,977 B2 | 5/2011 | Begelman et al. |
| 7,941,462 B2 | 5/2011 | Akinyemi et al. |
| 7,966,057 B2 | 6/2011 | Macaulay et al. |
| 7,970,189 B2 | 6/2011 | Buelow et al. |
| 7,983,459 B2 | 7/2011 | Begelman et al. |
| 8,057,539 B2 | 11/2011 | Ghione et al. |
| 8,073,221 B2 | 12/2011 | Kukuk et al. |
| 8,103,074 B2 | 1/2012 | Begelman et al. |
| 8,116,848 B2 | 2/2012 | Shahidi |
| 8,145,293 B2 | 3/2012 | Zhang et al. |
| 8,218,845 B2 | 7/2012 | Lynch et al. |
| 8,255,037 B2 | 8/2012 | Florent et al. |
| 8,255,038 B2 | 8/2012 | Zhang |
| 2011/0071404 A1* | 3/2011 | Schmitt ............... A61B 5/0066 600/479 |

* cited by examiner

CARDIAC ANALYSIS BASED ON VESSEL CHARACTERISTICS

CROSS REFERENCE TO RELATED APPLICATIONS

This application claims the benefit of priority, under 35 U.S.C. § 119, of U.S. Provisional Patent Application Ser. No. 61/753,024, filed on Jan. 16, 2013, titled "System for Cardiac Arrhythmia Based on Vessel Characteristics," the contents of which are hereby incorporated by reference in their entirety for all purposes.

BACKGROUND

Field

The embodiments described below relate to cardiac analysis based on blood vessel parameters determined from angiographic images.

Description

Many types of cardiac and/or circulatory diseases are serious and prevalent. These diseases include coronary artery disease and cardiac arrhythmias. It is therefore desirable to diagnosis these diseases early and efficiently, so that appropriate interventions and/or monitoring protocols may be implemented.

Known methods for diagnosing cardiac and/or circulatory diseases utilize electrophysiological signals (electrocardiogram (ECG) and multi-channel intra-cardiac electrograms (ICEG)) and hemodynamic signals. The signals are analyzed to detect and characterize cardiac events. A diagnosis may also be based on structural information determined from images (e.g., X-ray, ultrasound, CT). This structural information may include tissue morphology, blood flow, anatomy, blood flow blockage locations, and stent implant positions.

Electrophysiological and hemodynamic signals and signals are easily distorted and affected by electrical noise and bioartifacts, such as power line noise and patient movement. Moreover, interpreting images and signals to formulate a diagnosis requires extensive clinical experience and knowledge.

Systems are desired which provide efficient diagnosis of cardiac and/or circulatory diseases.

DETAILED DESCRIPTION

The following description is provided to enable any person in the art to make and use the described embodiments and sets forth the best mode contemplated for carrying out the described embodiments. Various modifications, however, will remain readily apparent to those in the art.

Figure 1:
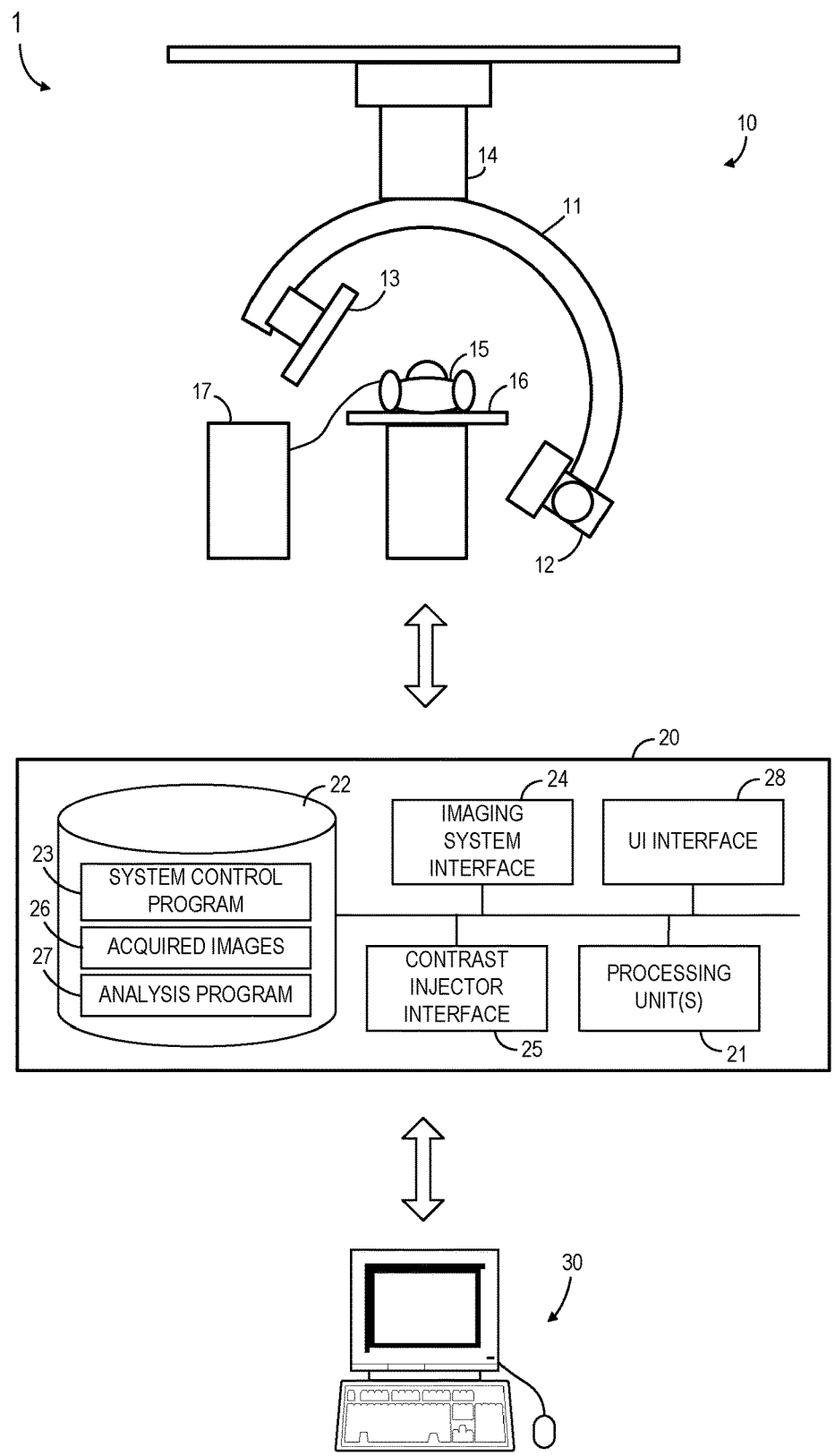
FIG. 1 illustrates a system according to some embodiments.

FIG. 1 illustrates system 1 according to some embodiments. System 1 includes imaging system 10, control and processing system 20, and operator terminal 30. Generally, and according to some embodiments, imaging system 10 introduces contrast medium into a patient volume and acquires images of the patient volume. Control and processing system 20 controls imaging system 10 and receives the acquired images therefrom. Control and processing system 20 processes the images as described below and provides output to terminal 30 for display thereby. Such processing may be based on user input received by terminal 30 and provided to control and processing system 20 by terminal 30.

According to the illustrated embodiment, imaging system 10 comprises C-arm 11 on which X-ray radiation source 12 and radiation detector 13 are mounted. C-arm 11 is mounted on support 14 and is configured to translate clockwise or counter-clockwise with respect to support 14. This translation rotates radiation source 12 and radiation detector 13 around a central volume while maintaining the physical relationship therebetween.

Embodiments are not limited to C-arm-based imaging systems. Imaging system 10 may comprise any system for acquiring images that is or becomes known. According to some embodiments, imaging system 10 may comprise an x-ray imaging system, a camera, a magnetic resonance imaging system, a positron emission tomography scanner, or a computed tomography imaging system. An image acquired by imaging system 10 includes one or more data values for each pixel of the image.

Radiation source 12 may comprise any suitable radiation source, including but not limited to an X-ray tube. In some embodiments, radiation source 12 emits electron, photon or other type of radiation having energies ranging from 50 to 150 keV.

Radiation detector 13 may comprise any system to acquire an image based on received x-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In some embodiments, radiation detector 13 converts received photons to electrical charge without requiring a scintillator layer. The photons are absorbed directly by an array of amorphous selenium photoconductors. The photoconductors convert the photons directly to stored electrical charge. Radiation detector 13 may comprise a CCD or tube-based camera, including a light-proof housing within which are disposed a scintillator, a mirror, and a camera.

The charge developed and stored by radiation detector 13 represents radiation intensities at each location of a radiation field produced by x-rays emitted from radiation source 12. The radiation intensity at a particular location of the radiation field represents the attenuative properties of tissues lying along a divergent line between radiation source 12 and the particular location of the radiation field. The set of radiation intensities acquired by radiation detector 13 may therefore represent a two-dimensional projection image of these tissues.

Contrast injector 17 may comprise any known device or devices suitable to controllably introduce contrast medium into a patient volume. Structures which contain contrast medium appear darker in x-ray images than they would otherwise appear. Contrast injector 17 may include a reservoir for each of one or more contrast media, and a patient interface such as medical-grade tubing terminating in a hollow needle.

System 20 may comprise any general-purpose or dedicated computing system. Accordingly, system 20 includes one or more processors 21 configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. One or more processing units 21 may execute system control program 23 to move C-arm 14, to cause radiation source 12 to emit radiation, to control detector 13 to acquire an image, to cause injector 17 to introduce contrast medium into a volume of patient 15, and to perform any other function. In this regard, system 20 includes imaging system interface 24 and contrast injector interface 25 for communication with system 10.

Images acquired from system 10 are stored in data storage device 22 as acquired images 26, in DICOM or another data format. Each acquired image 26 may be further associated with details of its acquisition, including but not limited to imaging plane position and angle, imaging position, radiation source-to-detector distance, patient anatomy imaged, patient position, contrast medium bolus injection profile, x-ray tube voltage, image resolution and radiation dosage.

Processing unit(s) 21 may execute analysis program 27 to process acquired images 26 as described herein. Generally, this processing may include reception of a first image of a blood vessel at substantially maximum blood pressure, reception of a second image of the blood vessel at substantially minimum blood pressure, determination of a first size of a region of the blood vessel based on the first image, determination of a second size of the region of the blood vessel based on the second image, and calculation of a parameter of the blood vessel based on the first size and the second size. As described below, the parameter may facilitate an efficient and accurate diagnosis.

Indications of the parameter and/or resulting diagnosis may be provided to terminal 30 via UI interface 28 of system 20. UI interface 28 may also receive input from terminal 30, which may be used to control the acquisition of images and/or the calculation of the parameter.

Terminal 30 may simply comprise a display device and an input device coupled to system 20. In some embodiments, terminal 30 is a separate computing device such as, but not limited to, a desktop computer, a laptop computer, a tablet computer, and a smartphone.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes images received from system 10. Embodiments are not limited to a single system performing each of these functions. For example, system 10 may be controlled by a dedicated control system, with the acquired images being provided to a separate image processing system over a computer network or via a physical storage medium (e.g., a DVD).

Figure 2:
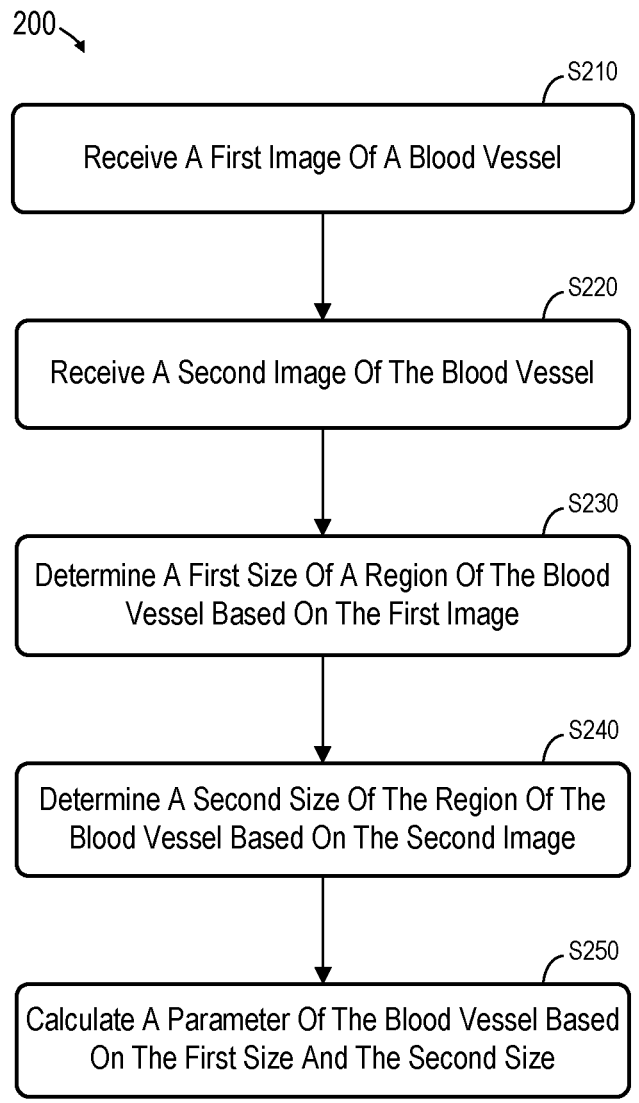
FIG. 2 is a flow diagram of a process according to some embodiments.

FIG. 2 is a flow diagram of process 200 according to some embodiments. Process 200 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape.

Initially, at S210, a first image of a blood vessel is received. The received image may have been acquired using any imaging system or technology that is or becomes known. In some embodiments, system 20 controls imaging system 10 to acquire an X-ray image of a blood vessel within patient 15, and receives the image therefrom at S210.

According to some embodiments, the first image is acquired while the blood vessel contains contrast media. For example, contrast injector 17 is operated to inject contrast media into an artery of patient 15, and the first image is acquired as the contrast media flows through the blood vessel. The contrast media causes the blood vessel to appear darker in the image than it would otherwise appear.

The first image depicts the blood vessel at a time of substantially maximum blood pressure. This time may be defined as period during which the blood vessel exhibits a maximum size. Size may refer to a diameter, a cross-sectional area, or another measure.

Figure 3:
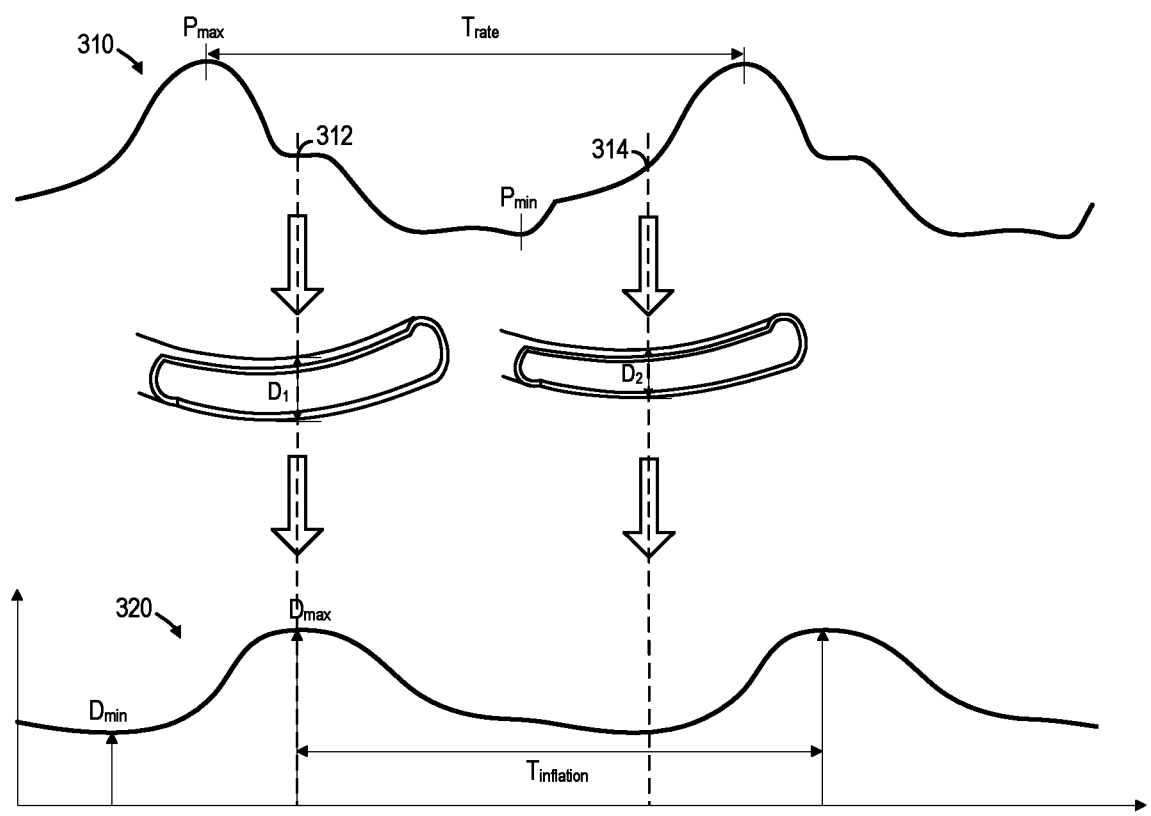
FIG. 3 illustrates changes in vessel size over time according to some embodiments.

FIG. 3 illustrates expansion and contraction of a blood vessel during cardiac cycling. Waveform 310 represents a hemodynamic blood pressure signal and waveform 320 plots the diameter of a particular portion of a blood vessel over time. As a cardiac chamber (atrium or ventricle) squeezes, blood flows into the coronary artery vessel with increasing pressure until a maximum pressure $P_{max}$. Shortly after $P_{max}$, the blood pressure within the blood vessel reaches a maximum, thereby causing the diameter of the blood vessel to simultaneously reach a maximum $D_{max}$.

A second image of the blood vessel is received at S220. The second image may also have been acquired using any imaging system or technology that is or becomes known, and acquired while the blood vessel contains contrast media. The second image depicts the blood vessel at a time of substantially minimum blood pressure, which may be defined as a period during which the blood vessel exhibits a minimum size. In this regard, FIG. 3 shows the diameter of the blood vessel reaching a minimum $D_{min}$ shortly after the occurrence of a minimum blood pressure $P_{min}$.

Next, at S230, a first size of a region of the blood vessel is determined based on the first image. Also, at S240, a second size of the region of the blood vessel is determined based on the second image. For purposes of the present example, it will be assumed that FIG. 3 illustrates the first image along with the determined first size $D_1$, and the second image along with the determined second size $D_2$. These sizes represent diameters of the region, but any other measure of size may be utilized at S230 and S240 according to some embodiments.

In the present example, vessel diameters may be determined at S230 and S240 using any known edge detection techniques such as, but not limited to, matching filter-based detection, wavelet analysis, maximum or minimum luminance detection of vessels comprising multiple pixels, edge detection of substantially contiguous vessel edge portions comprising multiple pixels based on change in luminance exceeding a threshold. After detecting the edges of the vessel's region of interest, the distance between the edges is measured to determine the diameter. In this regard, some embodiments may ensure that the first image and the second image depict the region of the vessel from a same projection angle, in order to ensure that differences between the first and second sizes are a result of vessel expansion/contraction.

According to some embodiments, S210 through S240 consist of receiving many images, determining a size of the region of the blood vessel in each image, and determining a maximum and minimum of the determined sizes. A waveform such as waveform 320 may then be generated may be generated based on a time stamp of each image and its corresponding region size.

According to some embodiments, the first image and the second image are DSA (Digital Subtraction Angiography) images. As is known in the art, DSA includes acquisition of a "mask image" of a region of interest prior to introducing contrast media into the region of interest. The mask image therefore represents background anatomic detail, and is subtracted from subsequently-acquired contrast media-enhanced images in order to remove the background anatomic detail from these images.

Next, at S250, a parameter associated with the blood vessel is calculated based on the first size and the second size. The parameter may relate the first size (i.e., a maximum size of the region of the vessel) with the second size (i.e., a minimum size of the region of the vessel). The parameter may therefore be useful for analyzing and characterizing cardiac functional abnormalities and arrhythmias.

In this regard, when blood flows within a coronary artery, different pressures cause blood vessel displacement resulting in the variation of the vessel section, size and degree of extension. If the vessel includes a blockage, for example due to fat or calcium accumulation, the vessel wall flexibility and ability to expand is reduced. Therefore, as discovered by the present inventors, the relation of vessel size during maximum expansion and vessel size during minimum expansion may be used to determine whether or not an abnormality is present.

In one embodiment, a vessel diameter ratio is determined at S250. Generally, the vessel diameter ratio may be represented as $D_m/D_n$. In the current example, $D_m=D_{max}$ and $D_n=D_{min}$. $D_m$ and $D_n$ may also or alternatively represent vessel diameters at points m and n within the heart cycle, such as but not limited to P wave, R wave, EoD, etc.

Other parameters may be determined at S250 according to some embodiments. For example, FIG. 3 shows $T_{rate}$, which is the time duration of the cardiac heart rate cycle, and $T_{inflation}$, which is the time duration of the vessel inflation cycle. Determination of these variables allows calculation of a vessel inflation-to-heart rate ratio $T_{inflation}/T_{rate}$. This ratio reflects coronary artery flexibility in contraction and recovery.

Figure 4:
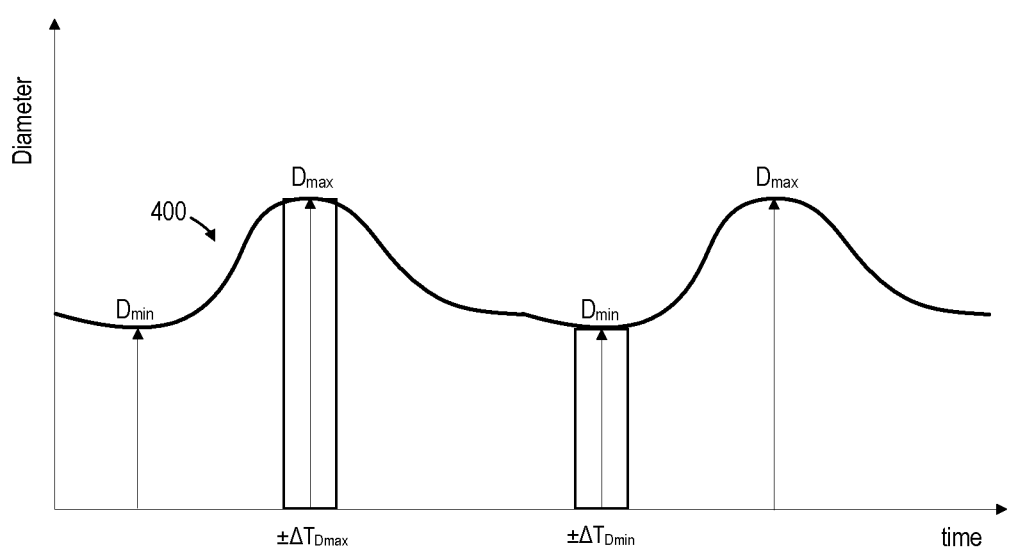
FIG. 4 illustrates determination of a blood vessel parameter according to some embodiments.

FIG. 4 illustrates diameter vs. time waveform 400 for describing calculation of a parameter at S250 according to some embodiments. $\pm \Delta T_{Dmax}$ is a duration associated with systole and during which the vessel expands to its largest size, and $\pm \Delta T_{Dmin}$ is a duration associated with diastole and during which the blood vessel contracts to its smallest size. These durations may be adaptively determined or designated by an operator. In some embodiments, these durations are used in conjunction with waveform 400 to calculate a vessel contraction and expansion energy ratio as follows:

$$\frac{\int_{i \in \Delta T_{Dmax}} |D(i)|^2}{\int_{i \in \Delta T_{Dmin}} |D(i)|^2},$$

where D(i) is a size of the region of interest at time i.

Regardless of the parameters determined at S250, these parameters may be combined into a universal ratio to improve the accuracy of analysis. For example, based on the ratios discussed above, a combined ratio may be determined as:

$$\Sigma_{i \in \theta} \beta_i \cdot Ratio_i$$

Where $\beta_i$ is a calculation coefficient in data combination, $Ratio_i$ represents different calculated ratios such as two or more of those discussed herein, and $\theta$ is a ratio database used for ratio calculations such as those discussed herein.

Figure 5:
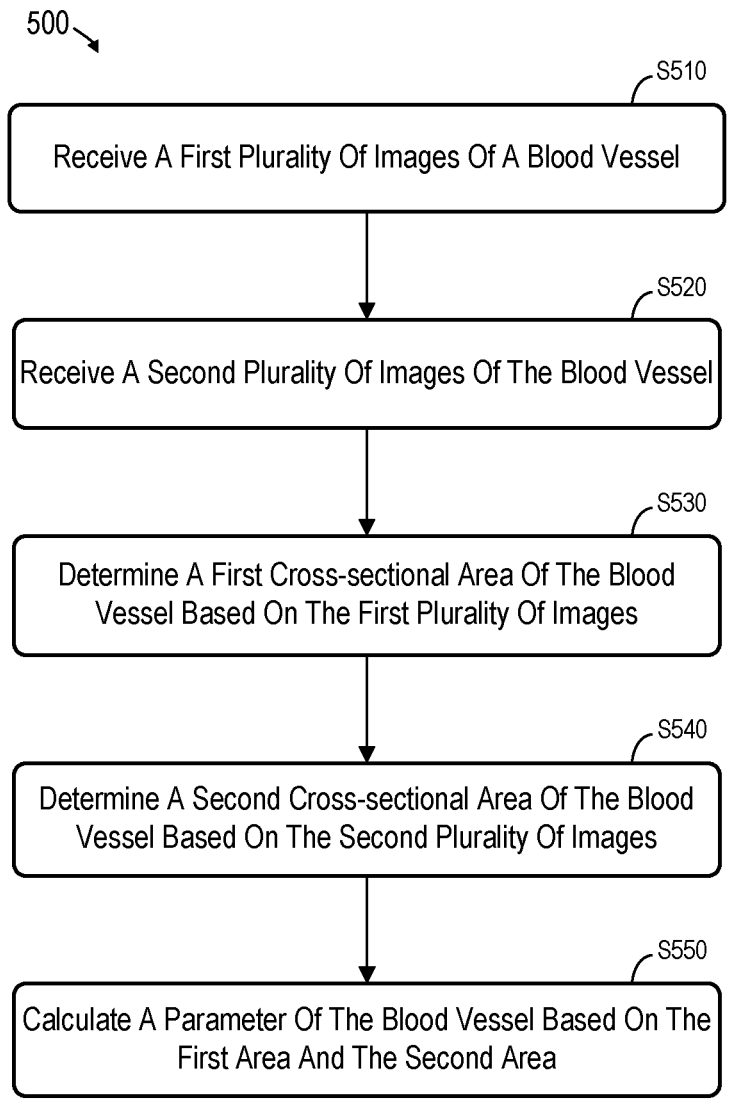
FIG. 5 is a flow diagram of a process according to some embodiments.

FIG. 5 is a flow diagram of process 500 according to some embodiments. Process 500 may be executed to determine a maximum cross-sectional area and a minimum cross-sectional area of a blood vessel.

A first plurality of images of a blood vessel is received at S510. The first plurality of images depict the blood vessel at a time of substantially maximum blood pressure. For example, system 20 may control imaging system 10 at S510 to acquire a plurality of X-ray images of a blood vessel within patient 15. As described above, the first plurality of images may be acquired while the blood vessel contains contrast media.

The first plurality of images are intended to provide a three-dimensional representation of a cross-sectional area of a region of the blood vessel in a particular state of expansion. Accordingly, each of the first plurality of images may be acquired at a same point of the hemodynamic blood pressure cycle (although at different absolute times) but at a different projection angle. A technique for determining the cross-sectional area of the region at the point of the hemodynamic blood pressure cycle based on first plurality of images is described below.

Next, at S520, a second plurality of images of the blood vessel is received. The second plurality of images may be acquired while the blood vessel contains contrast media. The second plurality of images depict the blood vessel at a time of substantially minimum blood pressure. Each of the second plurality of images may be acquired at a same point of the hemodynamic blood pressure cycle (although at different absolute times) but at a different projection angle.

Figure 6:
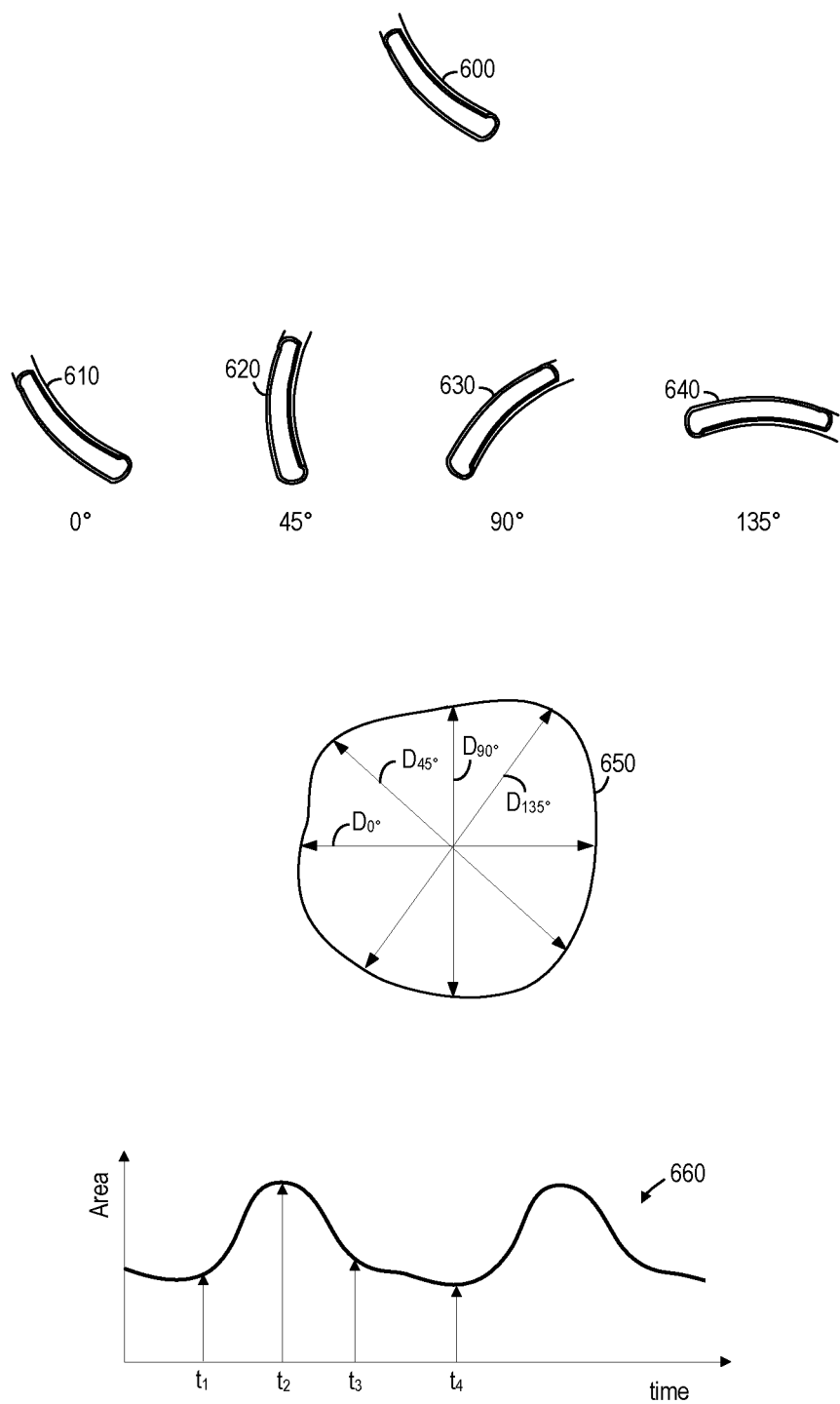
FIG. 6 illustrates determination of vessel size according to some embodiment.

A first cross-sectional area of a region of the blood vessel is determined based on the first plurality of images at S530, and a second cross-sectional area of the region of the blood vessel is determined based on the second plurality of images at S540. FIG. 6 illustrates S530 and S540 according to some embodiments.

FIG. 6 shows blood vessel 600 which is selected for analysis. Images 610 through 640 of blood vessel 600 have been received at S510, each of which represents a different projection angle. As mentioned above, each of images 610 through 640 also represents a same point of a hemodynamic blood pressure cycle.

A diameter of a region of interest is determined for each of images 610 through 640. The diameters may be determined as described above with respect to S230 and S240. Representation 650 is generated based on the determined diameters, labeled $D_{0°}$, $D_{45°}$, $D_{90°}$ and $D_{135°}$, and the area of representation 650 is determined. Accordingly, some embodiments provide efficient determination of the cross-sectional area using limited angular scanning.

According to some embodiments, the area is determined as:

$$S_{vessel} = \sum_{i \in N} \alpha_i \cdot \pi \left(\frac{D_i}{2}\right)^2$$

where N is the number of scanning angles (images), $\alpha_i$ is the coefficient of diameter i's contribution to the entire vessel section, and $D_i$ is the diameter of the ith image.

Waveform 660 is a plot of thusly-determined cross-sectional areas over time. The area plotted for a given time t is determined based on a plurality of images acquired at a hemodynamic (or heart rate) cycle point associated with time t.

A parameter associated with the blood vessel is calculated based on the first and second cross-sectional areas at S550. As described above, the parameter may therefore be useful for analyzing and characterizing cardiac functional abnormalities and arrhythmias present.

A vessel size ratio may be determined at S550. The vessel diameter ratio may be represented as $S_p/S_q$. In the current example, $S_p=S_{max}$ and $S_q=S_{min}$. $S_p$ and $S_q$ may also or alternatively represent vessel diameters at points p and q within the heart cycle, such as but not limited to P wave, R wave, EoD, etc.

Figure 7:
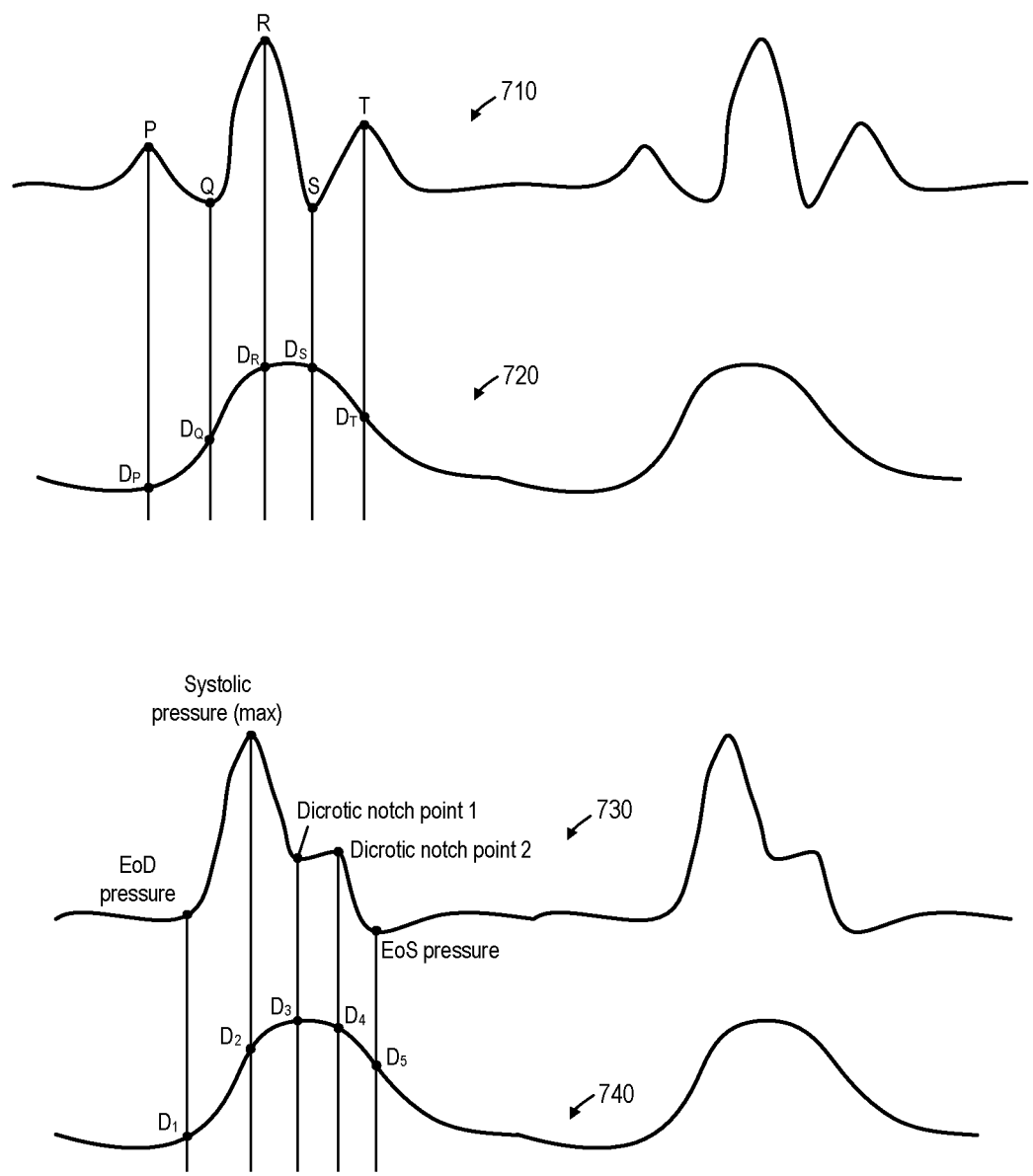
FIG. 7 illustrates gating of image acquisition according to some embodiments.

FIG. 7 illustrates waveforms for describing the gating of images according to some embodiments. For example, in the three-dimensional case of FIGS. 5 and 6, it is preferable to ensure that the vessel cross-sectional area is determined based on images representing a same point of a physiological cycle (e.g., heart rate, hemodynamic blood pressure, etc.). In the two-dimensional case, physiological signal-based gating provides additional information when evaluating the calculated parameters described herein to assess physiological function and conditions.

FIG. 7 illustrates two gating and synchronizing methods for vessel parameter and waveform signal segmentation and categorization. Waveform 710 is an ECG signal for segmenting vessel diameter/parameter waveform 720 using a P wave, R wave, etc. The vessel's mechanical properties are linked with an electrophysiological signal, via which the vessel parameters are determined during depolarization and repolarization. Specifically, parameters $D_P$, $D_Q$, $D_R$, $D_S$, and $D_T$ indicate vessel diameters for heart cycle points P wave, Q wave, R wave, S wave and T wave.

Waveform 730 is a hemodynamic blood pressure signal for segmenting vessel diameter/parameter waveform 740. Blood pressure-based gating may provide advantageous synchronization with the vessel size waveform. $D_1$, $D_2$, $D_3$, $D_4$, and $D_5$ represent vessel parameters (i.e., diameters) which correspond to a segmented blood pressure timing, EoD pressure, systolic pressure, dicrotic notch pressure 1, dicrotic notch pressure 2, and EoS pressure.

The processes described herein may be performed continuously, in real-time, and with respect to more than one blood vessel regions. Accordingly, some embodiments may generate a continuously-updated mapping of contraction and perfusion within an artery tree. This continuously-updated mapping may include vessel sizes and/or size-based parameters derived as described herein and may be displayed in real time. According to some embodiments, suspected abnormalities are indicated on the display, for example using color coding to indicate pathology type, severity, location, and/or timing.

Figure 8:
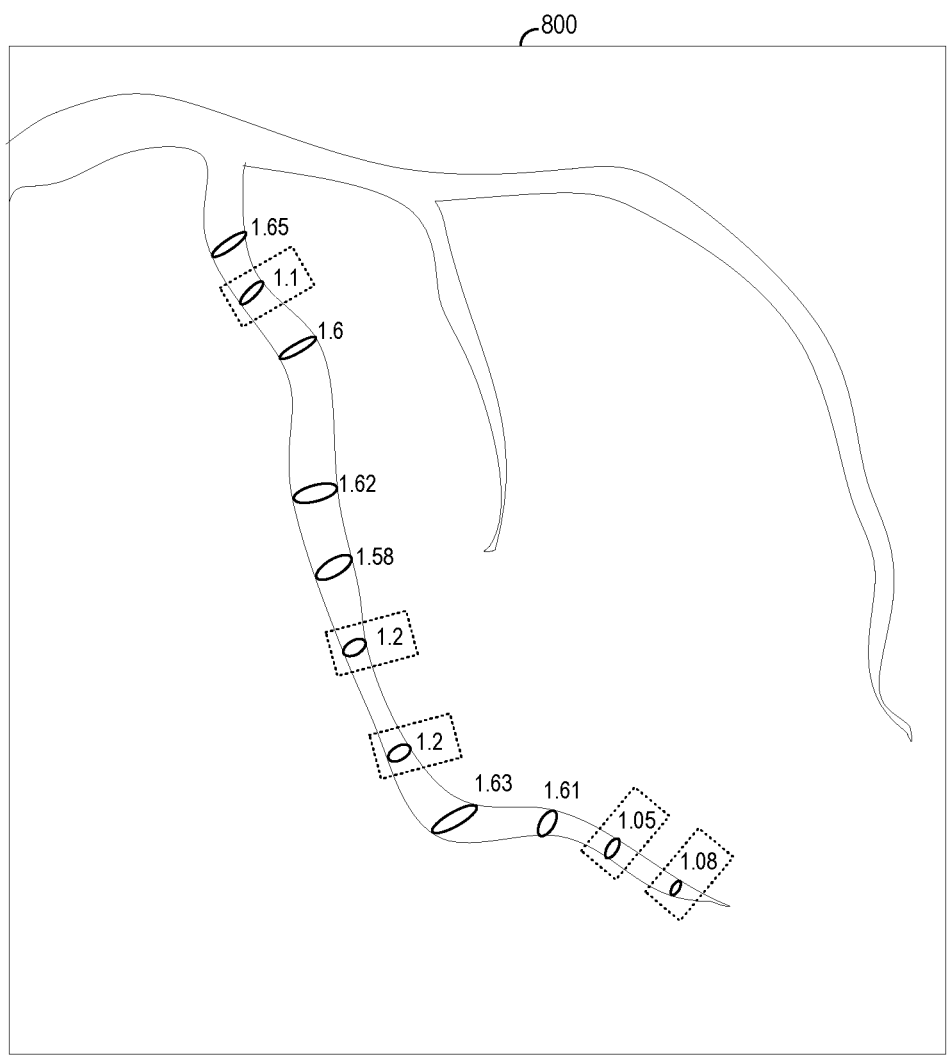
FIG. 8 illustrates display of blood vessel parameters according to some embodiments.

FIG. 8 illustrates continuously-updating image 800 of vessel ratios within a coronary artery according to some embodiments. Image 800 may be displayed to an operator of terminal 30. It will be assumed that, a diameter ratio of ~1.5-1.8 for systolic vs. diastolic timing is typical for a healthy coronary artery vessel. Image 800 highlights five potential myocardial ischemic locations, having systolic to diastolic vessel diameter ratios of 1.1, 1.2, 1.2, 1.05, and 1.08.

According to some embodiments, a vessel ratio variation (VRV) is calculated to provide a warning if a vessel ratio is more than 10%-20% of a mean value. This threshold may be adaptively adjusted and controlled based on the clinical application and noise level.

$$VRV = \frac{\text{Mean(Vessel ratio)}}{\text{STD(Vessel ratio)}}$$

Mean(Vessel ratio) is an average of vessel ratio values (e.g., over 5-10 cardiac cycles) and STD(Vessel ratio) is the standard deviation of the calculated vessel ratio values.

Figure 9:
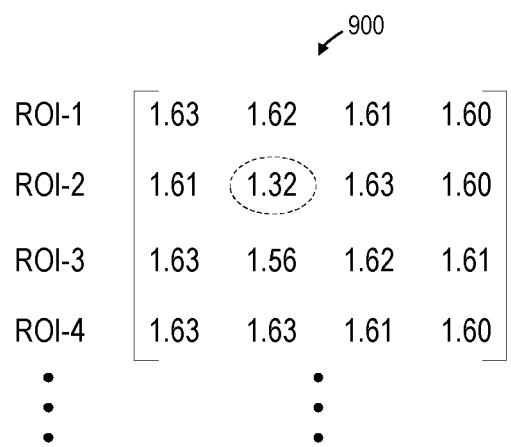
FIG. 9 illustrates display of blood vessel parameters according to some embodiments.

According to some embodiments, a matrix and submatrix of vessel ratios is generated and displayed for dynamic monitoring and evaluation of cardiac function. FIG. 9 illustrates cardiac coronary artery matrix 900 according to some embodiments. Different coronary arteries, such as LAD, RCA, and circumflex, are included in a matrix. Vessel points are located for each artery, therefore the matrix size depends on how many arteries and points are used. Each element in matrix 900 represents a potential pathological position in a specific artery or artery branch (e.g., second or third branch). Matrix elements of one artery or artery branches comprise a sub matrix. In the absence of a selection of a specific artery and point, the whole heart artery tree of systolic to diastolic ratio is analyzed and color coded or otherwise highlighted to indicate pathology type, severity, location and time point within a cardiac cycle. A blockage severity in a vessel may be determined by comparing its calculated value with a normal healthy mean value.

Highlights within matrix 900 may reflect any type of statistical analysis, tests and verification, such as t Test. Statistical analysis, cardiac pathology and malfunctions may be detected and characterized with predetermined threshold and accuracy confidences.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
   an interface configured to receive a first plurality of images of a blood vessel, and to receive a second plurality of images of the blood vessel; and
   a storage device configured to store program code executable by an image data processor to cause the image data processor to:
      determine a first plurality of respective sizes of a region of the blood vessel based on respective ones of the first plurality of images;
      determine a second plurality of respective sizes of a region of the blood vessel based on respective ones of the second plurality of images;
      calculate respective vessel contraction/expansion energy ratios based on at least one of the first plurality of respective sizes and at least one of the second plurality of respective sizes, the respective vessel contraction/expansion energy ratios each representing a ratio of an integral across multiple time regions for a duration associated with systole to the integral across multiple time regions for a duration associated with diastole;
      combine the respective vessel contraction/expansion energy ratios to form a universal ratio representing a summation of a plurality of respective products, each of the respective products being a product of each of the respective vessel contraction/expansion energy ratios multiplied by at least one calculation coefficient over increments of the blood vessel region;

analyze the respective vessel contraction/expansion energy ratios to characterize a presence of at least one of a cardiac functional abnormality and an arrhythmia;

display a result of the analysis on a display device of a terminal in communication with the image data processor, the display result including at least one of a mapping of an artery tree and a cardiac coronary artery matrix; and the artery tree mapping and the cardiac coronary artery matrix including an identification of a potential pathological position of at least one specific myocardial ischemic location in at least one of an artery and an artery branch, the myocardial ischemic location position based on a result of the analysis.

2. The system of claim 1, the artery tree depicting at least one of contraction and perfusion within an artery represented in the artery tree.

3. The system of claim 1, the image data processor further to analyze the respective vessel contraction/expansion energy ratios by comparison to a normal healthy mean value.

4. The system of claim 1, the image data processor further to determine from at least one of the first and at least one of the second plurality of respective sizes a respective blood vessel diameter ratio of the region of the blood vessel; and
apply the respective blood vessel diameter ratio in the analysis of the respective vessel contraction/expansion energy ratios.

5. The system of claim 1, including:
the first plurality of images acquired at substantially a same respective first point in a physiological cycle;
the second plurality of images acquired at substantially a same respective second point in a physiological cycle; and
determination of the first and the second plurality of respective sizes includes determination of one or more respective cross-sectional areas of the region of the blood vessel at the respective first and the respective second points.

6. The system of claim 5, wherein each of the plurality of images is associated with a different projection angle.

7. The system of claim 5, the image data processor further to calculate respective blood vessel inflation-to-heart rate ratios based on the respective cross-sectional areas at the respective first and the respective second points in the physiological cycle.

8. The system of claim 1, the first image depicting the blood vessel at substantially maximum blood pressure, and the second image depicting the blood vessel at substantially minimum blood pressure.

9. A method comprising:
receiving a first plurality of images of a blood vessel;
receiving a second plurality of images of the blood vessel;
determining a first plurality of respective sizes of a region of the blood vessel based on respective ones of the first plurality of images;
determining a second plurality of respective sizes of the region of the blood vessel based on respective ones of the second plurality of images;
calculating respective vessel contraction/expansion energy ratios based on at least one of the first plurality of respective sizes and at least one of the second plurality of respective sizes, the respective vessel contraction/expansion energy ratios each representing a ratio of an integral across multiple time regions for a duration associated with systole to the integral across multiple time regions for a duration associated with diastole;

combining the respective vessel contraction/expansion energy ratios to form a universal ratio representing a summation of a plurality of respective products, each of the respective products being a product of each of the respective vessel contraction/expansion energy ratios multiplied by at least one calculation coefficient over increments of the blood vessel region;

analyzing the respective vessel contraction/expansion energy ratios to characterize a presence of at least one of a cardiac functional abnormality and an arrhythmia;

displaying a result of the analysis on a display device of a terminal in communication with the image data processor, the display result including at least one of a mapping of an artery tree and a cardiac coronary artery matrix; and the artery tree mapping and the cardiac coronary artery matrix including an identification of a potential pathological position of at least one specific myocardial ischemic location in at least one of an artery and an artery branch, the myocardial ischemic location position based on a result of the analysis.

10. The method of claim 9, further comprising:
the artery tree depicting at least one of contraction and perfusion within an artery represented in the artery tree.

11. The method of claim 9, further comprising:
analyzing the respective vessel contraction/expansion energy ratios by comparison to a normal healthy mean value.

12. The method of claim 9, further comprising:
determining from at least one of the first and at least one of the second plurality of sizes a respective blood vessel diameter ratio of the region of the blood vessel; and
applying the respective blood vessel diameter ratio in the analysis of the respective vessel contraction/expansion energy ratios.

13. The method of claim 9, including:
acquiring the first plurality of images at substantially a same respective first point in a physiological cycle,
acquiring the second plurality of images at substantially a same respective second point in a physiological cycle; and
determining the first and the second plurality of respective sizes includes determining one or more respective cross-sectional areas of the region of the blood vessel at the respective first and the respective second points.

14. The method of claim 13, wherein each of the plurality of images is associated with a different projection angle.

15. The method of claim 13, further comprising:
calculating respective blood vessel inflation-to-heart rate ratios based on the respective cross-sectional areas at the respective first and the respective second points in the physiological cycle.

16. The method of claim 9, the first image depicting the blood vessel at substantially maximum blood pressure, and the second image depicting the blood vessel at substantially minimum blood pressure.

* * * * *